United States Patent [19]

Davidson

[11] Patent Number: 5,279,540
[45] Date of Patent: Jan. 18, 1994

[54] METHOD FOR REDUCING THE RISK OF ATHEROSCLEROSIS

[76] Inventor: Michael H. Davidson, 800 S. Wells, Suite M25, Chicago, Ill. 60607

[21] Appl. No.: 950,920

[22] Filed: Sep. 24, 1992

[51] Int. Cl.$^5$ .............................................. A61M 37/00
[52] U.S. Cl. ........................................... 604/4; 604/5
[58] Field of Search .................. 604/4, 5, 6, 27, 28, 604/29; 552/544; 436/71

[56] References Cited

U.S. PATENT DOCUMENTS

| | | | |
|---|---|---|---|
| 4,605,394 | 8/1986 | Shurkovich | 604/5 X |
| 4,692,411 | 9/1987 | Ghose | 604/5 X |
| 4,923,439 | 5/1990 | Seidel et al. | 604/5 X |

FOREIGN PATENT DOCUMENTS

| | | | |
|---|---|---|---|
| 139935 | 8/1984 | Japan | 604/4 |
| 1158969 | 7/1989 | Japan | 604/4 |
| 3289966 | 12/1991 | Japan | 604/5 |

OTHER PUBLICATIONS

"Plasma High Density Lipoprotein is Increased in Man when LDL is Lowered by LDL Pheresis" Parker et al., Proceedings, Natl. Academy of Sciences, vol. 83, pp. 777–781, Feb. 1986.

Brown et al, Molecular Basis of Lipid Transfer Protein Deficiency in a Family with Increased High-Density Lipoproteins, Nature, vol. 342, Nov. 23, 1989.

Barter, Enzymes Involved in Lipid and Lipoprotein Metabolism, Current Opinion in Lipidology 1990, 1:518–523.

Cholesteryl Ester Transfer Protein, The Lancet, vol. 338: Sep. 14, 1991.

Inazu et al, Increased High-Density Lipoprotein Levels Caused by a Common Cholesteryl-Ester Transfer Protein Gene Mutation, The New England Journal of Medicine, vol. 323, No. 18, pp. 1234–1238.

Yamashita et al, Accumulation of Apolipoprotein E--rich High Density Lipoproteins in Hyperalphalipoproteinemic Human Subjects with Plasma Cholesteryl Ester Transfer Protein Deficiency, J. Clin. Invest., vol. 86, 9–90, 688–695.

Hesler et al, Structure–Function Analysis of Plasma Cholesteryl Ester Transfer Protein by Protease Digestion and Expression of cDNA Fragments in *Escherichia coli*, The Journal of Biological Chemistry, vol. 264, No. 19, Issue of Jul. 5, 1989, pp. 11317–11325.

Yen et al, Inhibition of Cholesteryl Ester Transfer Protein Activity by Monoclonal Antibody, J. Clin. Invest., vol. 83, Jun. 1989, pp. 2018–2024.

Lagrost et al, Role of Cholesteryl Ester Transfer Protein (CETP) in the HDL Conversion Process as Evidenced by Using Anti-CETP Monoclonal Antibodies, Journal of Lipid Research, vol. 31, 1990, pp. 1569–1575.

Savolainen et al, Increased High-Density Lipoprotein Cholesterol Concentration in Alcoholics is Related to Low Cholesteryl Ester Transfer Protein Activity, European Journal of Clinical Investigation (1990) 20, pp. 593–599.

Horwitz, Apheresis Adsorbs LDL Only, Medical Tribune, date unknown.

*Primary Examiner*—Robert A. Hafer
*Assistant Examiner*—Sam Rimell
*Attorney, Agent, or Firm*—Hill, Steadman & Simpson

[57] ABSTRACT

A method for reducing the risk of atherosclerosis in a patient at risk of same comprising the steps of removing cholesterol ester transfer protein from blood of the patient to reduce the plasma CETP levels in the patient. In an embodiment, the method includes the step of passing the patient's plasma through an apheresis machine to remove at least some of the plasma cholesterol ester transfer protein.

15 Claims, No Drawings

METHOD FOR REDUCING THE RISK OF ATHEROSCLEROSIS

BACKGROUND OF THE INVENTION

The present invention relates generally to treatments for atherosclerosis. More specifically, the present invention relates to methods of reducing the risk of atherosclerosis.

Cardiovascular disease is the leading cause of death in the United States. In the United States, of a population of 226.5 million in 1980, 551,400 died of ischemic heart disease and 169,500 died of cerebrovascular causes related to arterial disease. See Merck Manual, 15th Edition, p. 386.

Atherosclerosis is a form of arteriosclerosis marked by the formation of atheromas. The disease causes the lumen of an artery to become narrowed or blocked (occluded). The atheroma obstructs circulation by protruding into the arterial lumen. The narrowing of the artery restricts blood flow to the organ that is nourished by the artery. The reduced blood flow results in a deterioration of the organ to the point wherein the organ can be permanently damaged unless the blockage of blood flow is removed. When an artery that serves the heart is narrowed or blocked, the pathological process results in a heart attack.

The relationship between hypercholesterolemia, abnormal lipoprotein profiles, and atherogenesis has been well defined. A major risk factor of atherosclerosis is elevated serum lipids. See Merck Manual, 15th Edition, p. 386. Studies have also demonstrated that elevated levels of high density lipoproteins (HDL) - cholesterol are negatively correlated to the incidence of coronary heart disease. See, Yamashita et al, "Accumulation of Apolipoprotein E-Rich High Density Lipoproteins in Hyperalphalipoproteinemic Human Subjects with Plasma Cholesterol Ester Transfer Protein Deficiency", Journal of Clinical Investigation, Vol. 86, September 1990, 688–695.

Cholesterol is an essential component of the membranes of every human cell, necessary for tissue repair and other functions. The amount of cholesterol entering the circulation each day, however, greatly exceeds the essential requirements. There is no system for the cholesterol catabolism in the peripheral tissues. Accordingly, excess cholesterol arriving at the periphery must be returned to the liver if it is to be eliminated. The process by which the cholesterol is returned to the liver is termed "reverse cholesterol transport." High-density lipoprotein has been implicated in reverse cholesterol transport. See, Cholesterol Ester Transfer Protein, The Lancet, Vol. 338, Sep. 14, 1991, pp. 666–667.

Although HDL levels are known to be decreased by obesity, cigarette smoking, male sex, and diets high in polyunsaturated fat, the mechanisms of variations of HDL levels in populations are poorly understood. Inazu et al, "Increase High-Density Lipoprotein Levels Caused By A Common Cholesterol-Ester Transfer Protein Gene Mutation", The New England Journal of Medicine, Nov. 1, 1990, p. 1234–1238.

In vivo, cholesterol ester transfer protein is believed to be central to cholesterol transport in human plasma. Despite the potential benefits of the cholesterol pathway, in terms of control and regulation of cholesterol transport, there is considerable disadvantage because cholesterol ester transfer protein can convert the non-atherogenic HDL into VLDL. VLDL is the precursor for LDL that has been strongly implicated in the pathogenesis of atherosclerosis. It has been reported that the combination of sodium oleate and CETP promotes a major redistribution of cholesterol ester from HDL to LDL. See, Barter. "Enzymes Involved in Lipid and Lipoprotein Metabolism", Current Opinion in Lipidology, 1990, 1:518–523. See also, Brown et al. "Molecular Basis of Lipid Transfer Protein Deficiency in a Family With Increased High-Density Lipoproteins", Nature, Vol. 342, Nov. 23, 1989, pp. 448–451 ("[t]he plasma cholesterol ester transfer protein (CETP) catalyses the transfer of cholesterol ester from HDL to other lipoproteins and therefore might influence HDL levels.").

SUMMARY OF THE INVENTION

The present invention provides a method for reducing the risk of atherosclerosis in a patient at risk of same. Pursuant to the present invention, cholesterol ester transfer protein is removed from the blood (plasma) of the patient. This will result in reduced plasma levels of CETP and increased plasma levels of HDL in the patient. HDL cholesterol is believed to have an anti-atherosclerotic effect on the patient.

Pursuant to an embodiment of the present invention, the cholesterol ester transfer protein is removed utilizing an apheresis process.

Additionally, the present invention provides a column for removing cholesterol ester transfer protein.

In an embodiment, the present invention can be used in combination with an LDL-immunophoresis process to insure the levels of plasma LDL are suppressed and the levels of plasma HDL are elevated.

The present invention can also be used in conjunction with cholesterol lowering drugs and/or low fat diets. In this regard, the present invention can be part of a therapy for treating coronary artery disease.

An advantage of the present invention is that it provides a method for reducing the risk of atherosclerosis.

A further advantage of the present invention is that it provides a method for increasing plasma levels of HDL.

Moreover, an advantage of the present invention is that it provides a column for removing cholesterol ester transfer protein.

Still further, an advantage of the present invention is that it can be used in conjunction with processes for removing plasma LDL.

An advantage of the present invention over the use of LDL apheresis alone is that LDL cholesterol levels are decreased and HDL cholesterol levels are increased resulting in an improved anti-atherosclerotic lipid profile with less frequent use of apheresis therapy.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for reducing the risk of atherosclerosis in a patient at risk of same. Although high-density lipoproteins (HDL) have an anti-atherosclerotic effect, cholesterol ester transfer protein is believed to assist in exchanging cholesterol ester from HDL to low density lipoproteins (LDL) which have been implicated with respect to atherosclerosis. In patients at risk of atherosclerosis, this transfer of cholesterol ester from HDL to LDL can increase the risk of atherosclerosis. Additionally, in certain patients having reduced levels of HDL, increased levels of cholesterol ester transfer protein can worsen the plasma ratio of HDL to LDL.

Pursuant to the present invention, a method is provided for limiting the risk of atherosclerosis. The method comprises the step of removing from the blood of a patient at risk of atherosclerosis, cholesterol ester transfer protein to reduce the plasma level of CETP. The levels of plasma CETP should be reduced by at least approximately 50%. Most preferably, the levels of plasma CETP are reduced by at least approximately 75%. In an embodiment, levels of CETP are preferably reduced by at least approximately 75% and maintained at levels that are reduced by 70% to 75% for at least one week.

A variety of methods can be used to remove the cholesterol ester transfer protein. A variety of methods can also be used to inhibit the activity of the cholesterol ester transfer protein.

In a preferred embodiment, an apheresis machine is used to remove the cholesterol ester transfer protein. An example of an apheresis machine that can be used is the blood cell separator machine produced by Baxter International or the apheresis machine produced by Kaneka (Liposorber).

To remove the cholesterol ester transfer protein, a column is used. The column would include anti-CETP antibodies. The column comprises an extracorporeal device that is used in conjunction with an apheresis machine that separates blood plasma from the formed elements of blood. After separation of plasma and cellular elements of blood, the plasma is passed through the column then recombined with the cellular elements before return to the body. The column of this invention is optimized to remove CETP from plasma with a high degree of specificity while leaving all other soluble elements of plasma unchanged from that found in circulating plasma. It is further optimized so that the time required for apheresis treatment is minimized.

The active element of the column is an antibody against human CETP that has the characteristics of high avidity and tight binding of the protein CETP. The antibody (anti-human cholesterol ester transfer protein) may be polyclonal in nature such as that obtained by standard antibody raising and harvesting protocols used in suitable animal species such as rabbits, sheep or goats. The antibody is rigorously purified from the animal plasma prior to application in the device of this invention to assure the safety of the subjects treated. The antibody may be monoclonal in nature such as that obtained from monoclonal lymphocyte cells of mice or humans, the cells maintained in vitro can be stimulated to produce antibodies to human CETP which can be harvested and purified from the cell culture medium.

The antibody is immobilized to a solid insoluble matrix by covalent binding of the antibody protein to the solid matrix in a manner that preserves the antibody specificity for binding CETP. A variety of chemical reactions for covalently bonding proteins to solid matrices are known to those skilled in the art. Most commonly proteins are coupled to high molecular weight carbohydrate polymers such as Sepharose, Agarose or cellulose. The most commonly used reagent for chemical linkage of proteins to carbohydrate polymers is cyanogen bromide. Also useful are derivatives of these carbohydrates that are activated with a reactive epoxy moiety at the distal end of an aliphatic hydrocarbon to act as a "spacer" separating the protein from the carbohydrate polymer.

Other solid supports made from chemically synthesized polymers such as acrylic acid polymer prepared in the physical form of beads can be activated with an oxirane moiety. Proteins such as the antibody to CETP can be bonded to this activated polymer to form a suitable column material for the column of this invention.

Typically, the chemically bound protein (antibody) occurs at a concentration in the insoluble polymer of from 2 mg to about 15 mg of protein per ml of fully hydrated polymer. The amount of anti-CETP antibody bound to the polymer in the column device must be sufficient to remove essentially all of the CETP in the plasma in a single passage through the column. Since the total amount of CETP in the plasma of a 70 kg subject is from 5 mg to about 25 mg of protein, an antibody excess of from 2 to 10, fold on a molecular weight basis is required for efficient and rapid removal of CETP from the plasma as it passes through and over the polymer. The total volume of hydrated polymer containing the bound anti-CETP antibody would be no less than about 20 ml and preferably about 50 ml.

The active polymeric material is enclosed in a suitable medical grade plastic or metal column with a design maximized for rate of plasma flow through the column and for efficient and uniform distribution of plasma flowing over and through the insoluble matrix containing the antibody. Such column devices have been described in U.S. Pat. No. 4,432,871.

The column may be prepared and used as multiple use devices that can be used several times in the same patient after suitable cleaning and purification after each use. The column may also be prepared as a disposable device that is discarded after a single use.

In an alternative configuration the column of this invention can be prepared by chemically linking the binding antibody to the surface of a non-porous membrane so that the antibody is available to bind and retain CETP from plasma as it flows over the membrane surface. For efficient removal of CETP from plasma a high surface to volume configuration is required such as hollow fibers or pleated sheets. For efficient removal of CETP the antibody should be bound at a surface density of from about 25 mg to 150 mg per square meter of membrane surface.

Patients having low levels of plasma HDL or at risk of atherosclerosis can be placed on an apheresis procedure utilizing such an anti-CETP column. This should result in the reduction of plasma CETP levels providing increased levels of plasma HDL and reducing the risk of atherosclerosis.

It is envisioned that the typical patients who would be treated would include those who have a severe defect in HDL metabolism that results in an HDL concentration of about 35 mg/dl or less, that are at high risk of development of premature atherosclerosis. Similarly, patients who present combined low HDL-cholesterol and high LDL-cholesterol such as patients with familial combined hyperlipidemia (a genetic disorder associated with premature severe coronary artery disease would also benefit from the present invention).

These patients would typically be subjected to weekly, or bi-weekly, pheresis. The treatment would continue for several years to potentially life long therapy. The treatment would consist of an acute phase of therapy with weekly apheresis therapy for several weeks to several months combined with drug therapy. A longer term therapy consisting of apheresis therapy on a less frequent basis combined with a spectrum of other less invasive therapies such as drug and diet therapy would be instituted once the plasma lipid profile had stabilized at more nearly normal levels.

Of course, the present invention can be used with other treatments designed to reduce the risk of, or treat, atherosclerosis. For example, the present invention can be used in conjunction with cholesterol lowering drugs and/or low fat diets.

Recently, LDL-immunophoresis has been used to selectively remove LDL. See, H. Mabuchi, "Use of LDL Apheresis in Management of Hypercholesterolemia", Current Opinions in Lipidology, Vol. 1, No. 1, pp. 43-47 (1990).

In this regard, an apheresis system, the Liposorber LA-15 System (Kaneka American Corporation) has been used to remove plasma LDL in hypercholesterolemia patients.

Pursuant to the present invention, CETP-apheresis can be used in conjunction with LDL-apheresis. By reducing plasma CETP levels in conjunction with LDL levels, the transfer of spared cholesterol ester in HDL to LDL will be reduced, therefore, HDL plasma levels should be increased to a greater extent.

An example of such a procedure is as follows:

Suitable cannula are introduced into the left and right cubital veins of the patient. Anticoagulation is achieved with use of heparin alone or with a combination of citrate and heparin. The blood cell separation device is preprimed with the patient's blood and the cell separation machine is started.

After stabilization of the operation of the cell separation machine the flow of plasma is diverted to flow through the CETP-antibody containing column. A plasma flow rate of 25-50 ml/minute is maintained until approximately 2000-3000 ml of plasma has been passed over the immunoabsorbing column. The plasma flow through the column is then stopped and one column volume of sterile physiological saline is passed over the column and the remaining plasma and saline rinse are returned to the patient with the last of the separated blood cells.

Of course, if desired, other methods of reducing plasma LDL levels can be used in conjunction with the present invention.

By way of example, and not limitation, contemplative examples of the present invention will now be given.

EXAMPLE NO. 1

Sixty (60) ml of hydrated Cyanogen Bromide-Activated Sepharose 6 MB was suspended in dilute phosphate buffered saline (PBS) and approximately 700 mg of goat anti-human CETP antibody was added in 20 ml of PBS. The activated Sepharose was gently resuspended in the antibody containing PBS solution.

After an appropriate reaction time, an amount of Sepharose gel and supernatant was transferred to the final column device to prepare a column containing 50 ml of gel. Excess supernatant was allowed to pass through the gel followed by two column volumes of dilute PBS. This was followed by three column volumes of dilute PBS. This was followed by two column volumes of 5 mM ethanolamine to block excess active groups on the gel. A final wash of three column volumes of dilute PBS was added and the reaction device was closed and sealed.

All materials used were tested for sterility and for pyrogenicity. All operations were conducted in a laminar flow hood. The final column effluent was tested for sterility, pyrogenicity, and for the presence of unbound antibody.

A small test column (approximately 5 ml of gel volume) was prepared from the excess reacted gel to test the activated gel for CETP binding capacity. Ten (10) ml of human plasma containing 2 micrograms of CETP/ml was passed over the test column to verify the binding capacity of the immobilized antibody. Complete removal of CETP was verified by the absence of CETP activity in the column effluent. Removal of bound CETP was verified by eluting the CETP from the column with appropriate buffered chaotrophic agents and measuring the CETP protein by immunoassay.

A candidate for CETP and/or LDL apheresis was evaluated for venous access. Since venous access was deemed to be limited, a double lumen indwelling catheter was surgically placed into the subclavian vein. The patient received weekly apheresis treatments with plasma flowing first through an LDL-antibody column then through a CETP-antibody column. Weekly treatments were continued for 14 weeks. Each treatment including patient and machine preparation required three to four hours. Baseline and post-treatment lipoproteins profiles and CETP activity levels were determined at each treatment. During the week, the patient was continued on cholesterol lowering drug therapy (a HMG-CoA inhibitor) and a very low fat diet (less than 10% of calories from fat).

In addition to lowering LDL-cholesterol levels and CETP levels by immunoapheresis therapy, the HMG-CoA inhibitor was used to maintain the lowered LDL-cholesterol levels and the very low fat diet was used to prevent the exposure of the arterial wall to potentially atherogenic chylomicron remnants and to further lower LDL-cholesterol levels. In this patient, CETP apheresis resulted in increased levels of HDL-cholesterol and low levels of LDL-cholesterol. Target goals of therapy were to reduce LDL-cholesterol below 50 mg/dl and to maintain HDL-cholesterol levels above 50 mg/dl. Maintenance of these target levels of lipoproteins for 6 to 12 months would result in a marked reduction in coronary luminal stenosis.

The lipid profile results and CETP levels over the 14 weeks of weekly therapy are shown in tabular form below:

| LDL-CHOLESTEROL, HDL-CHOLESTEROL, AND CETP LEVELS DURING COMBINED LDL-APHERESIS AND CETP-APHERESIS | | | |
|---|---|---|---|
| TREATMENT WEEK | LDL-CHOLESTEROL MG/DL | HDL-CHOLESTEROL MG/DL | CETP MG/L |
| 1 PRE | 285 | 32 | 5.2 |
| POST | 200 | 31 | 1.4 |
| 2 PRE | 264 | 37 | 3.9 |
| POST | 177 | 35 | 1.2 |
| 3 PRE | 186 | 41 | 3.7 |
| POST | 149 | 39 | 1.3 |
| 4 PRE | 181 | 44 | 3.7 |
| POST | 127 | 43 | 1 |
| 5 PRE | 185 | 46 | 3.6 |
| POST | 124 | 44 | 1.1 |
| 6 PRE | 179 | 47 | 2.9 |
| POST | 125 | 45 | 1 |
| 7 PRE | 164 | 49 | 2.7 |
| POST | 110 | 48 | 0.9 |

LDL-CHOLESTEROL, HDL-CHOLESTEROL, AND CETP LEVELS DURING COMBINED LDL-APHERESIS AND CETP-APHERESIS
-continued

| TREATMENT WEEK | | LDL-CHOLESTEROL MG/DL | HDL-CHOLESTEROL MG/DL | CETP MG/L |
|---|---|---|---|---|
| 8 | PRE | 151 | 51 | 2.5 |
|   | POST | 103 | 48 | 0.85 |
| 9 | PRE | 128 | 53 | 2.4 |
|   | POST | 92 | 49 | 0.75 |
| 10 | PRE | 125 | 55 | 2.1 |
|    | POST | 94 | 54 | 0.6 |
| 11 | PRE | 114 | 58 | 1.8 |
|    | POST | 86 | 57 | 0.5 |
| 12 | PRE | 107 | 57 | 1.2 |
|    | POST | 80 | 56 | 0.45 |
| 13 | PRE | 88 | 57 | 1.1 |
|    | POST | 68 | 55 | 0.45 |
| 14 | PRE | 74 | 58 | 1.1 |
|    | POST | 50 | 56 | 0.45 |

EXAMPLE NO. 2

A patient with a low HDL-cholesterol and documented atherosclerosis.

A 40 year old status post interior wall myocardial infarction with a lipid profile of:

| Total cholesterol | 170 mg/dl |
|---|---|
| Triglycerides | 150 mg/dl |
| HDL-cholesterol | 25 mg/dl |
| LDL-cholesterol | 115 mg/dl |
| Total cholesterol/HDL ratio | 6.8 |

This patient has a severe defect in HDL metabolism resulting in premature development of atherosclerosis.

Weekly CETP pheresis pursuant to the present invention would result in a CETP deficiency and a subsequent increase in HDL-cholesterol. CETP pheresis is expected to result in a 50%–100% increase in the HDL-cholesterol level which should reduce the risk of future atherosclerotic complications.

EXAMPLE NO. 3

A coronary artery disease patient with combined low HDL-cholesterol and high LDL-cholesterol.

A 50 year old female with angina pectoris; 3 vessel coronary disease with a lipid profile of:

| Total cholesterol | 350 mg/dl |
|---|---|
| Triglycerides | 250 mg/dl |
| HDL-cholesterol | 35 mg/dl |
| LDL-cholesterol | 265 mg/dl |
| Total cholesterol/HDL ratio | 10.4 |

This patient has familial combined hyperlipidemia; a genetic disorder associated with premature coronary disease.

Weekly CETP and LDL apheresis combined should result in a 50% increase in HDL-C and a 50% decrease in LDL-C. Medication with a HMG-CoA reductase inhibitors such as lovastatin given concomitantly on a daily basis should reduce the rebound in LDL-C levels during the week between LDL apheresis treatments. The addition of a very low fat diet should also reduce the risk for further atherosclerotic development.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for reducing the risk of atherosclerosis in a patient at risk of same comprising the steps of:
    removing cholesterol ester transfer protein from blood of the patient by passing the blood through an apheresis machine having an anti-CETP column to reduce plasma CETP levels in the patient; and
    administering to the patient a cholesterol lowering drug.

2. The method of claim 1 wherein plasma CETP level is reduced to a level at least approximately 50% less than the plasma CETP level prior to treatment in the patient.

3. A method for reducing the risk of atherosclerosis in a patient at risk of same comprising the steps of:
    passing the patient's plasma through an apheresis machine including an anti-CETP column wherein the column includes at least twice the antibodies having an affinity for CETP, on a molecular weight basis, as the projected plasma CETP of the patient; and
    removing through apheresis, at least some of the cholesterol ester transfer protein from the patient's plasma.

4. The method of claim 3 including the step of removing sufficient cholesterol ester transfer protein (CETP) to reduce the level of plasma CETP by at least approximately 50%.

5. The method of claim 3 wherein the plasma CETP levels are reduced to a level that is at least 75% less than the plasma CETP levels prior to treatment.

6. The method of claim 3 including the step of administering to the patient a cholesterol lowering drug.

7. The method of claim 3 including the steps of on a regular basis removing at least some of the cholesterol ester transfer protein from the patient's plasma.

8. A method for reducing the risk of atherosclerosis in a patient at risk of same comprising the steps of:
    removing cholesterol ester transfer protein from blood of the patient by passing the blood through an apheresis machine having an anti-CETP column to reduce plasma CETP levels in the patient; and
    maintaining the patient on a low fat diet that is intended to reduce the intake of cholesterol.

9. The method of claim 8 wherein the plasma CETP levels are reduced to a level that is at least 75% less than the plasma CETP level prior to treatment.

10. A method for reducing the risk of atherosclerosis in a patient at risk of same comprising the steps of:
    passing the patient's plasma through an apheresis machine including an anti-CETP column that includes at least approximately 20 ml of antibodies having an affinity for CETP; and
    removing through apheresis, at least some of the cholesterol ester transfer protein from the patient's plasma.

11. A method for reducing the risk of atherosclerosis in a patient at risk of same comprising the steps of:
    passing the patient's plasma through an apheresis machine including a column for removing LDL to remove at least some of LDL present in the plasma; and passing the patient's plasma through an apheresis machine including a column that includes antibodies having an affinity for CETP for removing cholesterol ester transfer protein to remove at least some of the cholesterol ester protein present in the plasma.

12. The method of claim 16 wherein the LDL is removed first.

13. The method of claim 11 wherein the cholesterol ester transfer protein is removed first.

14. The method of claim 11 wherein a sufficient amount of cholesterol ester transfer protein (CETP) is removed to reduce plasma CETP levels at least approximately 50%.

15. The method of claim 11 including the step of administering to the patient a cholesterol lowering drug.

* * * * *